(12) United States Patent
Flagle et al.

(10) Patent No.: US 7,628,804 B2
(45) Date of Patent: Dec. 8, 2009

(54) PROSTHETIC VALVE WITH VESSEL ENGAGING MEMBER

(75) Inventors: Jacob A. Flagle, Bloomington, IN (US); Brian C. Case, Bloomington, IN (US); Andrew K. Hoffa, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 713 days.

(21) Appl. No.: 10/857,403

(22) Filed: May 28, 2004

(65) Prior Publication Data
US 2004/0254636 A1    Dec. 16, 2004

Related U.S. Application Data

(60) Provisional application No. 60/473,911, filed on May 28, 2003.

(51) Int. Cl.
*A61F 2/06* (2006.01)
(52) U.S. Cl. ............ 623/1.24; 623/1.26; 623/2.38
(58) Field of Classification Search ........ 623/1.24, 623/1.26, 2.12–2.19, 2.38, 2.39, 2.4, 2.41
See application file for complete search history.

(56) References Cited

U.S. PATENT DOCUMENTS

| | | | | |
|---|---|---|---|---|
| 2,682,057 A * | 6/1954 | Lord | | 623/2.38 |
| 3,464,065 A * | 9/1969 | Cromie | | 623/2.38 |
| 3,581,426 A * | 6/1971 | Miller | | 43/22 |
| 4,470,157 A * | 9/1984 | Love | | 623/2.15 |
| 4,626,255 A * | 12/1986 | Reichart et al. | | 623/2.13 |
| 4,680,131 A * | 7/1987 | Busch et al. | | 510/311 |
| 4,705,516 A * | 11/1987 | Barone et al. | | 623/2.39 |
| 4,856,510 A * | 8/1989 | Kowalewski | | 128/207.15 |
| 5,103,817 A * | 4/1992 | Reisdorf et al. | | 128/207.15 |
| 5,322,062 A * | 6/1994 | Servas | | 128/207.14 |
| 5,713,953 A | 2/1998 | Curcio et al. | | |
| 5,855,602 A * | 1/1999 | Angell | | 623/2.11 |
| 5,891,195 A * | 4/1999 | Klostermeyer et al. | | 623/1.26 |
| 5,937,861 A * | 8/1999 | Augustine | | 128/207.15 |
| 5,947,995 A * | 9/1999 | Samuels | | 606/200 |
| 6,106,550 A * | 8/2000 | Magovern et al. | | 623/2.38 |
| 6,312,465 B1 | 11/2001 | Griffin | | |
| 6,494,909 B2 | 12/2002 | Greenhalgh | | |
| 6,506,197 B1 * | 1/2003 | Rollero et al. | | 606/148 |
| 6,508,833 B2 | 1/2003 | Pavcnik | | |
| 6,733,525 B2 * | 5/2004 | Yang et al. | | 623/2.18 |
| 7,041,132 B2 * | 5/2006 | Quijano et al. | | 623/2.11 |
| 7,172,625 B2 * | 2/2007 | Shu et al. | | 623/2.41 |

(Continued)

FOREIGN PATENT DOCUMENTS

FR    2828091    2/2003

(Continued)

*Primary Examiner*—Paul Prebilic
(74) *Attorney, Agent, or Firm*—Buchanan Intellectual Property Office LLC

(57) ABSTRACT

Medical devices for implantation in a body vessel are provided. Each medical device comprises a main body, a valve, and a vessel engaging member. The vessel engaging member is disposed on an outer surface of the main body. Kits including a plurality of vessel engaging members for use with one or more valve members are also provided. The vessel engaging members have varying radial dimensions, allowing assembly of medical devices having varying radial dimensions. Methods of treating a patient using medical devices according to the invention are also provided.

20 Claims, 5 Drawing Sheets

U.S. PATENT DOCUMENTS

| | | | |
|---|---|---|---|
| 2003/0078617 A1* | 4/2003 | Schwartz et al. | 606/230 |
| 2004/0015232 A1 | 1/2004 | Salazar et al. | |
| 2004/0080352 A1 | 4/2004 | Noda et al. | |
| 2004/0204692 A1* | 10/2004 | Eliasen | 604/288.02 |
| 2004/0254636 A1* | 12/2004 | Flagle et al. | 623/1.24 |
| 2007/0198097 A1* | 8/2007 | Zegdi | 623/23.68 |
| 2007/0255394 A1* | 11/2007 | Ryan | 623/1.24 |

FOREIGN PATENT DOCUMENTS

| | | |
|---|---|---|
| WO | 96/40011 | 12/1996 |
| WO | 00/64380 | 11/2000 |
| WO | 01/12105 | 2/2001 |
| WO | WO 01/66190 A2 | 9/2001 |
| WO | WO 2004/080352 A1 * | 3/2004 |

* cited by examiner

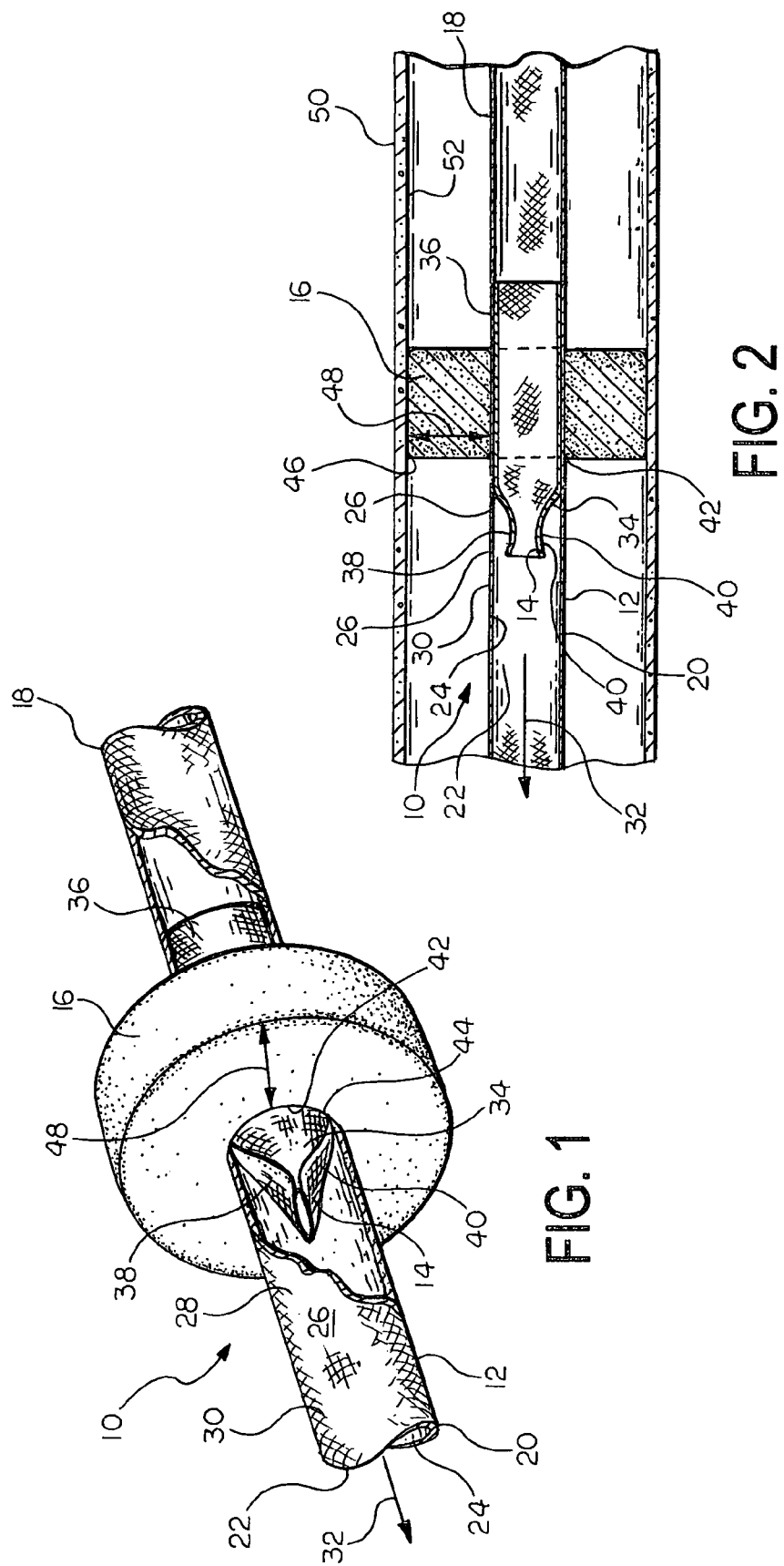

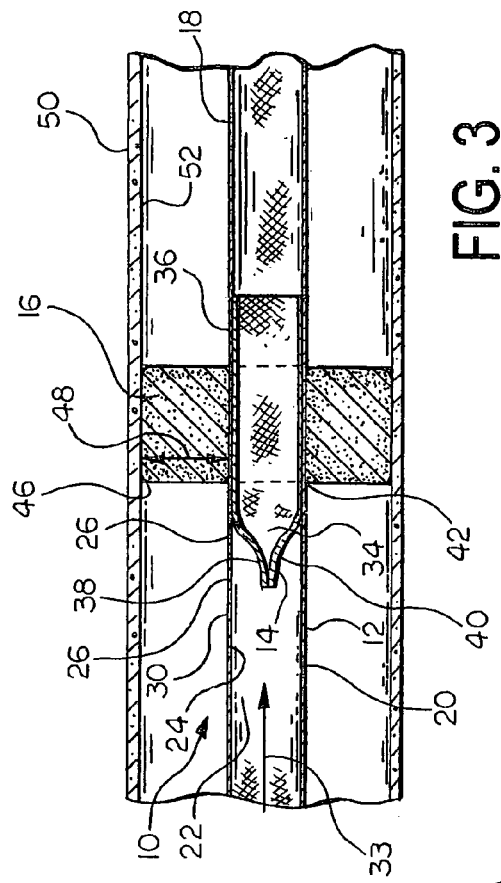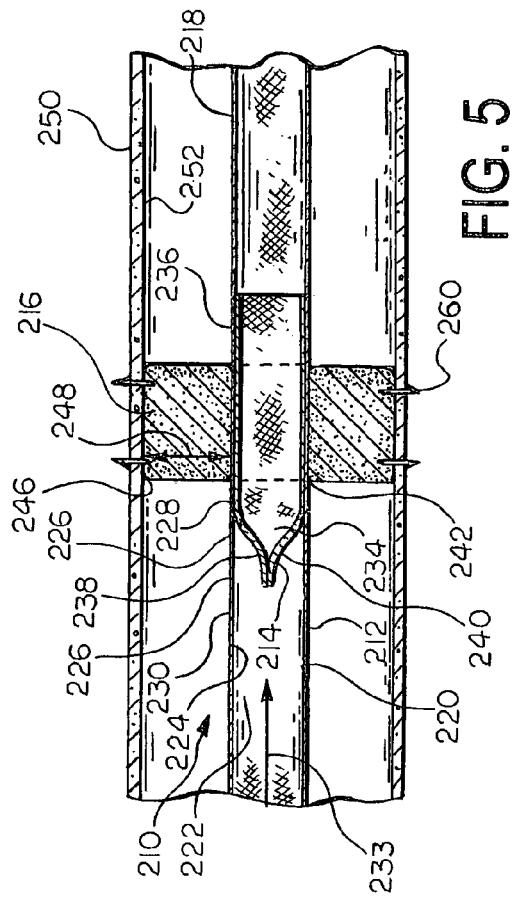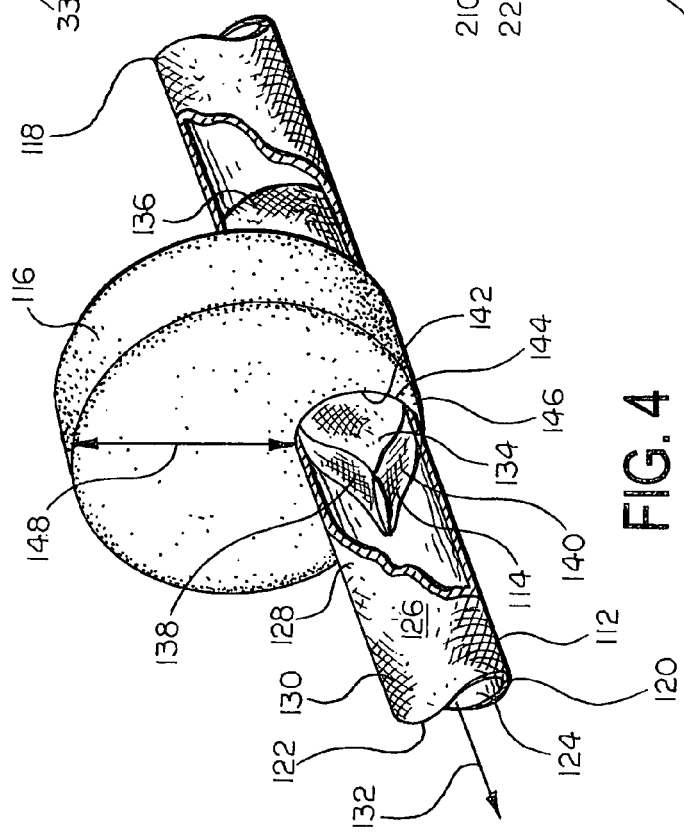

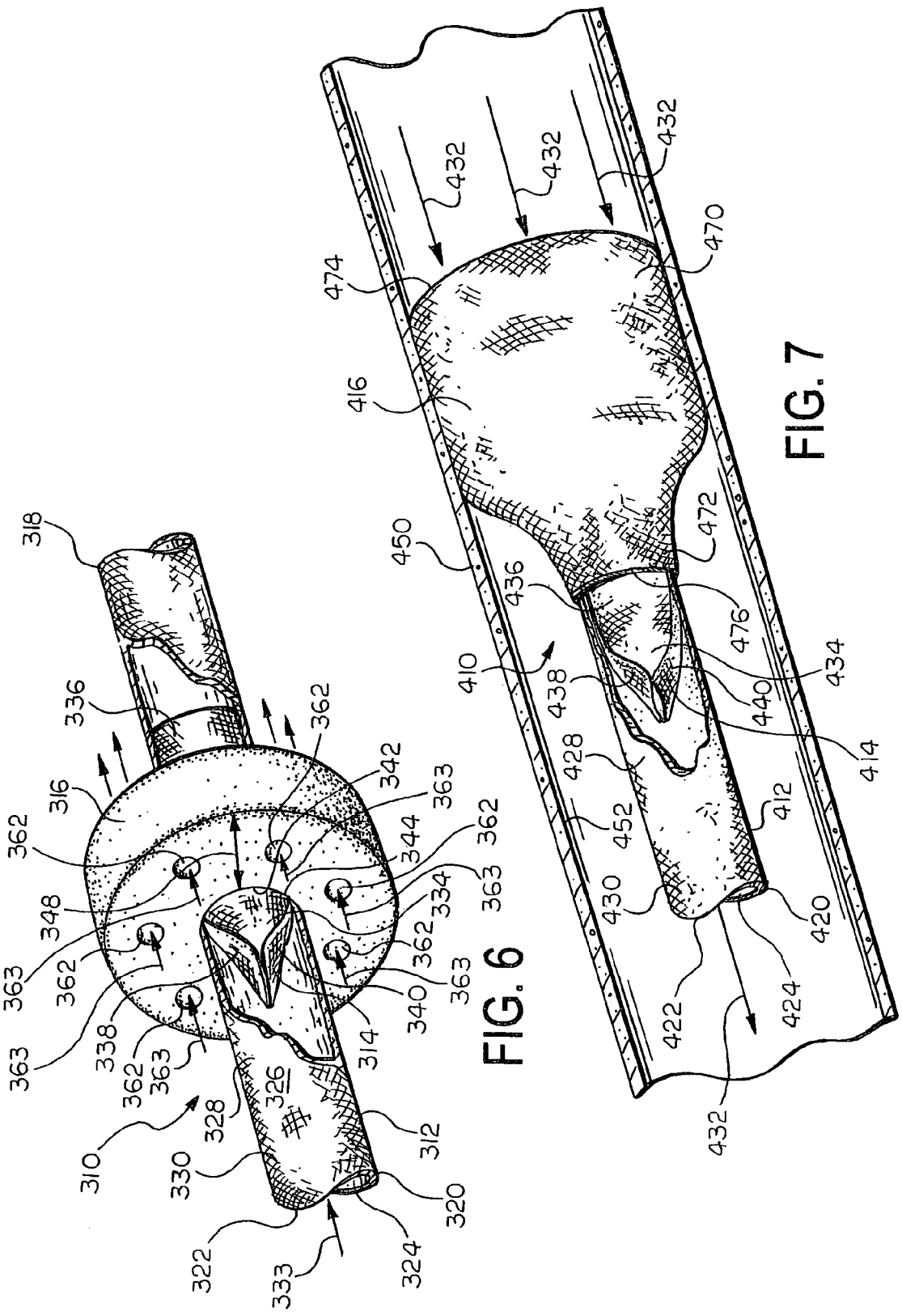

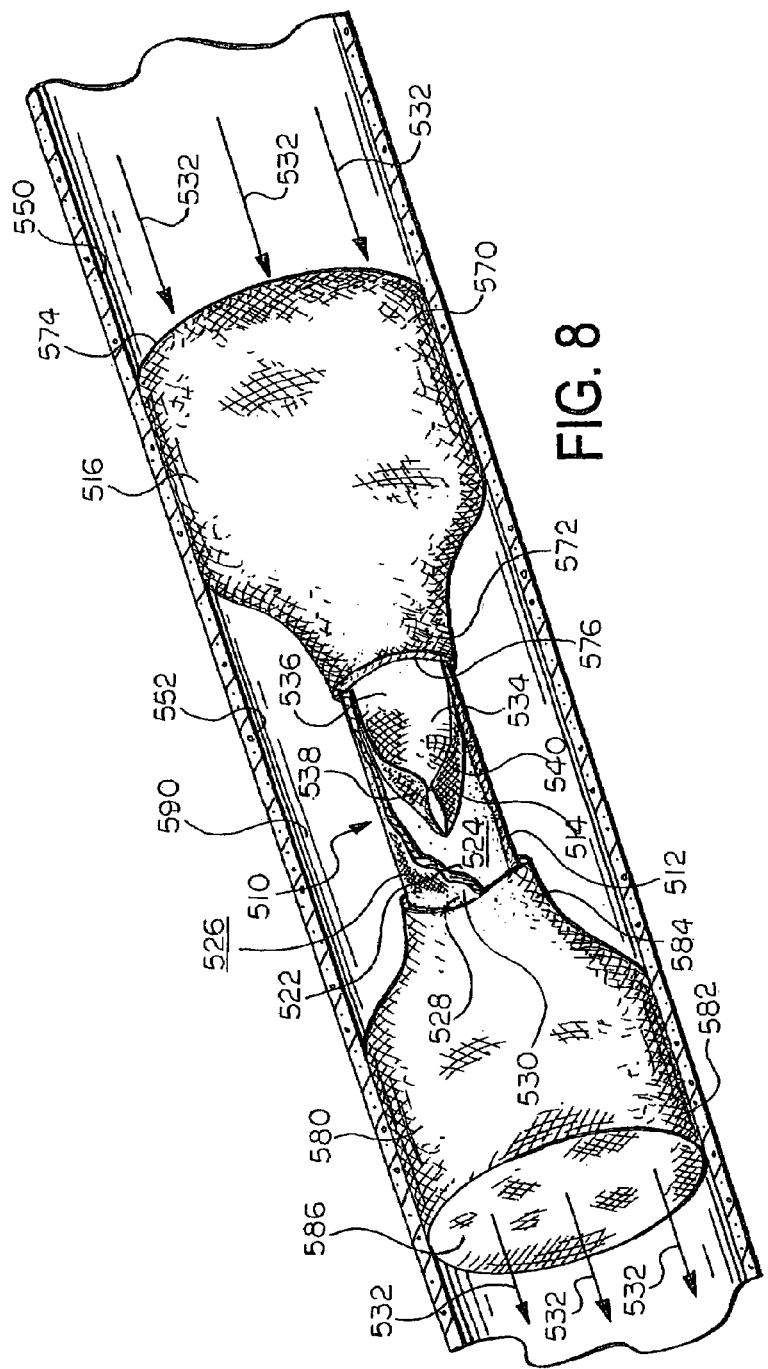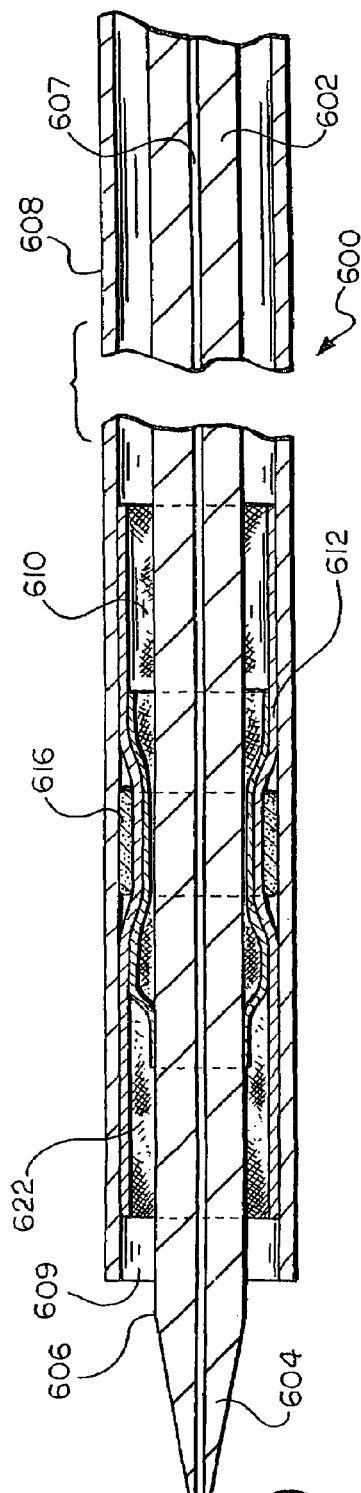
FIG. 8
FIG. 9

PROSTHETIC VALVE WITH VESSEL ENGAGING MEMBER

CROSS-REFERENCE TO RELATED APPLICATION

This application claims priority to U.S. Provisional Application Ser. No. 60/473,911 filed on May 28, 2003, the entire disclosure of which is hereby incorporated into this disclosure in its entirety.

FIELD OF THE INVENTION

The present invention relates to medical devices. More particularly, the invention relates to medical devices for implantation in a body vessel.

BACKGROUND OF THE INVENTION

Many vessels in animals transport fluids from one bodily location to another. Frequently, fluid flows in a unidirectional manner along the length of the vessel. Varying fluid pressures over time, however, can introduce a reverse flow direction in the vessel. In some vessels, such as mammalian veins, natural valves are positioned along the length of the vessel and act as one-way check valves that open to permit the flow of fluid in the desired direction, and quickly close upon a change in pressure, such as a transition from systole to diastole, to prevent fluid flow in a reverse direction, i.e., retrograde flow.

While natural valves may function for an extended time, some may lose effectiveness, which can lead to physical manifestations and pathology. For example, venous valves are susceptible to becoming insufficient due to one or more of a variety of factors. Over time, the vessel wall may stretch, affecting the ability of the valve leaflets to close. Furthermore, the leaflets may become damaged, such as by formation of thrombus and scar tissue, which may also affect the ability of the valve leaflets to close. Once valves are damaged, venous valve insufficiency may be present, which can lead to discomfort and possibly ulcers in the legs and ankles.

Current treatments for venous valve insufficiency include surgical techniques in which valves are bypassed or replaced with autologous sections of veins with competent valves. These techniques are generally undesirable because they represent a relatively invasive approach to treating valve insufficiency.

Minimally invasive techniques and instruments for placement of intraluminal medical devices have developed over recent years. A wide variety of treatment devices that utilize minimally invasive technology has been developed and includes stents, stent grafts, occlusion devices, infusion catheters and the like. Minimally invasive intravascular devices have especially become popular with the introduction of coronary stents to the U.S. market in the early 1990's. Coronary and peripheral stents have been proven to provide a superior means of maintaining vessel patency, and have become widely accepted in the medical community. Furthermore, the use of stents has been extended to treat aneurisms and to provide occlusion devices, among other uses.

Recently, prosthetic valves have been developed that use a support frame such as a stent. Frequently, a graft member is attached to the support frame and provides a valve function to the device. For example, the graft member can be in the form of a leaflet that is attached to a stent and movable between first and second positions. In a first position, the valve is open and allows fluid flow to proceed through a vessel in a first direction, and in a second direction the valve is closed to prevent fluid flow in a second, opposite direction. An example of this type of prosthetic valve is described in commonly owned U.S. Pat. No. 6,508,833, to Pavcnik for a MULTIPLE-SIDED INTRALUMINAL MEDICAL DEVICE, which is hereby incorporated by reference in its entirety. In other examples of prosthetic valves, a tube that terminates in valve portions is attached to one or more support frames to form a valve. The valve portions open to permit fluid flow in a first direction in response to fluid pressure on one side of the portions, and close to prevent fluid flow in a second, opposite direction in response to fluid pressure on opposite sides of the portions. An example of this configuration is provided in U.S. Pat. No. 6,494,909 to Greenhalgh for AN ENDOVASCULAR VALVE, which is hereby incorporated by reference in its entirety.

One challenge in the development of prosthetic valves is the sizing of the valves. The body vessels in which the valves are placed exist in various sizes and configurations in any given patient population. For example, prosthetic venous valves are designed for placement within a vein of a patient. These body vessels exist in a variety of sizes and have a high degree of elasticity. Accordingly, there is a need for medical devices, kits, and methods that are capable of being adapted to vessels of various sizes.

SUMMARY OF EXEMPLARY EMBODIMENTS OF THE INVENTION

The invention provides medical devices for implantation in a body vessel.

In one exemplary embodiment, a medical device according to the invention comprises a main body having an outer surface and defining a passageway therethrough. A valve is disposed in the passageway and adapted to permit fluid flow through the passageway in a first direction and substantially prevent fluid flow through the passageway in a second, opposite direction. A vessel engaging member is disposed on the outer surface of the main body.

In one exemplary embodiment, a medical device according to the invention comprises a main body having an outer surface and defining a passageway therethrough. A valve is disposed in the passageway and adapted to permit fluid flow through the passageway in a first direction and substantially prevent fluid flow through the passageway in a second, opposite direction. Means for engaging said body vessel are disposed on the outer surface of the main body.

In one exemplary embodiment, a medical device according to the invention comprises a prosthetic valve having a stent and a tubular valve body disposed in a passageway defined by the stent. A vessel engaging member is disposed around the stent.

The invention also provides delivery devices. In one embodiment, a delivery device according to the invention comprises an elongate member comprising a distal end and a prosthetic valve according to the invention disposed on the distal end. A sheath can be disposed around the prosthetic valve and the elongate member.

The invention also provides kits. In one embodiment, a kit according to the invention comprises a valve member comprising a main body defining a passageway and a valve disposed in the passageway. The valve is adapted to permit fluid flow through the passageway in a first direction and substantially prevent fluid flow through the passageway in a second, opposite direction. The kit also comprises a plurality of vessel engaging members. Each of the plurality of vessel engaging members comprises inner and outer edges and defines an opening adapted to receive the main body of the valve member. Each of the plurality of vessel engaging members has a dimension extending from the inner edge to the outer edge. Two of the plurality of vessel engaging members comprise different dimensions.

The invention also provides methods of treating a patient. In one embodiment, a method of treatment according to the invention comprises providing a kit according to the invention; determining an inner diameter of a body vessel at a point of treatment; selecting a vessel engaging member having a suitable dimension; disposing the main body of a valve member in the opening of the vessel engaging member to form a medical device; and implanting the medical device at the point of treatment.

The invention includes other embodiments within the scope of the claims, and variations of all embodiments, and is limited only by the claims made by the applicants. Additional understanding of the invention can be obtained by referencing the detailed description of exemplary embodiments of the invention, below, and the appended drawings.

BRIEF DESCRIPTION OF THE DRAWINGS

FIG. 1 is a perspective view, partially broken away, of a medical device according to a first embodiment of the invention.

FIG. 2 is a sectional view of the medical device of FIG. 1 within a body vessel with the valve in an open configuration.

FIG. 3 is a sectional view of the medical device of FIG. 1 within a body vessel with the valve in a closed configuration.

FIG. 4 is a perspective view, partially broken away, of a medical device according to a second embodiment of the invention.

FIG. 5 is a sectional view of a medical device according to a third embodiment of the invention within a body vessel.

FIG. 6 is a perspective view, partially broken away, of a medical device according to a fourth embodiment of the invention.

FIG. 7 is a perspective view, partially broken away, of a medical device according to a fifth embodiment of the invention within a body vessel.

FIG. 8 is a perspective view, partially broken away, of a medical device according to a sixth embodiment of the invention within a body vessel.

FIG. 9 is a sectional view of a catheter according to an embodiment of the invention.

DETAILED DESCRIPTION OF EXEMPLARY EMBODIMENTS OF THE INVENTION

Figure 11:
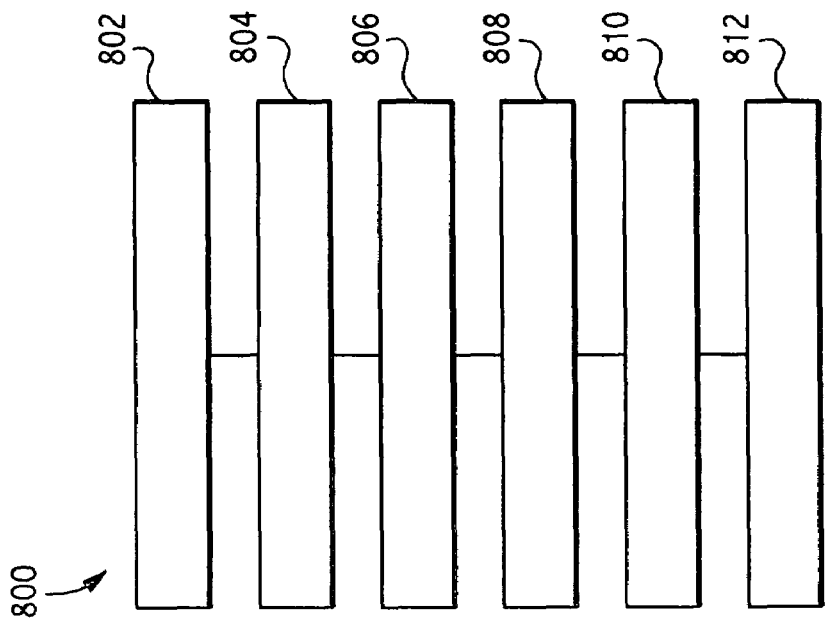
FIG. 11 is a flowchart of a method of treating a patient according to an embodiment of the invention.

The following detailed description and appended drawings describe and illustrate various exemplary embodiments of the invention. The description and drawings serve to enable one skilled in the art to make and use the invention, and are not intended to limit the scope of the invention, or its protection, in any manner.

The invention provides medical devices for implantation in a body vessel, catheters, kits, and methods of treating patients that utilize medical devices according to the invention.

FIGS. 1 through 3 illustrate a medical device 10 according to a first embodiment of the invention. The device 10 is an implantable medical device that comprises a main body 12, a valve 14, and a vessel engaging member 16.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

The main body 12 has proximal 18 and distal 20 ends and defines a passageway 22 extending between the ends 18, 20. The passageway 22 provides a path for fluid flow through main body 12. An inner surface 24 of the main body 12 bounds the passageway 22, and an outer surface 26 defines the exterior of the main body 12. The main body 12 and the passageway 22 need not have any particular length, and the lengths can be optimized for a particular point of treatment.

Any suitable structure defining a passageway can be utilized as the main body 12. Examples of suitable structures include, without limitation, composite tubular structures, such as polymeric tubular structures, wire form structures, such as self-expandable stents, and balloon expandable stents, such as those cut from tubular members. Self-expandable and balloon expandable stents have a first, unexpanded configuration and a second, expanded configuration, which facilitates delivery and implantation by percutaneous techniques.

The structure of the main body 12 can be formed from a variety of materials, and need only be biocompatible, or able to be made biocompatible. Examples of suitable materials include, without limitation, stainless steel, nickel titanium (NiTi) alloys, e.g., Nitinol, other shape memory and/or superelastic materials, polymers, and composite materials. A resorbable material can also be used for the main body 12. As used herein, the term "resorbable" refers to the ability of a material to be absorbed into a tissue and/or body fluid upon contact with the tissue and/or body fluid. A number of resorbable materials are known in the art, and any suitable resorbable material can be used. Examples of suitable types of resorbable materials include resorbable homopolymers, copolymers, or blends of resorbable polymers. Specific examples of suitable resorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein.

The main body 12 need not have any particular configuration, and the tubular configuration of the illustrated embodiment is exemplary in nature. The specific configuration and composition of the structure chosen for the main body 12 will depend on several factors, including the size of the body vessel in which the medical device 10 will be implanted, the quantity of fluid passed through the body vessel under normal physiological conditions, the quantity of fluid desired to be passed through the main body 12 following implantation in the body vessel, and the desired implantation technique. Those skilled in the art can determine an appropriate structure for the main body 12 based on all or some of these factors, and other factors.

The structure chosen for the main body 12 should provide a structure to which the valve 14 can be attached. The valve 14 can be attached to the main body 12 in any suitable manner, such as by attachment elements, including sutures and adhesives, as well as friction, and other suitable fastening mechanisms and/or techniques. The main body 12 can include a portion 28 of the outer surface 26 that is impervious to fluid flow. When present, the impervious portion 28 can extend to the same axial length as the valve 14. Also, the impervious portion 28 can extend axially beyond the valve 14. This configuration encourages fluid to flow through the valve 14 and minimizes fluid flow that passes through the body vessel in which the device 10 is implanted without passing through the valve 14. The impervious portion 28 can be a portion of the main body 12 itself, such as a portion of a tubular member, or it can be a separately attached member. Also, an impervious material can be used to form the valve 14 to achieve the desired result.

As best illustrated in FIG. 1, a graft member 30 can be attached to main body 12. In this embodiment, the graft member 30 comprises the impervious portion 28 and extends from the proximal end 18 to the distal end 20 of the main body 12. Any suitable graft material can be used to form the graft member 30. The specific material chosen should provide the impervious portion 28, if desired. Examples of suitable graft materials include polymers, such as polyurethane and polytetrafluoroethylene (PTFE), and natural materials, such as an extracellular matrix (ECM) material or other bioremodellable material. Small intestine submucosa (SIS) is particularly well-suited for use as the graft member 30 at least due to its ability to remodel and become incorporated into host tissue. Also, the graft member 30 can have any suitable configuration, including tubular and sheet configurations, and can be attached to any surface of the main body 12, including either or both of the inner 24 and outer 26 surfaces. Similar to the valve 14, the graft member 30 can be attached to the main body 12 in any suitable manner.

The valve 14 is disposed in the passageway 22 and is adapted to permit fluid flow through the passageway 22 in a first direction 32 and substantially prevent fluid flow through the passageway 22 in a second, opposite direction 33, i.e., retrograde flow. The valve 14 can be any suitable valve that is able to provide the desired ability to permit fluid flow in the first direction 32 and substantially prevent fluid flow in the second, opposite direction 33. Examples of suitable valves include valves formed by attachment of one or more valve leaflets to a support frame, such as the prosthetic valves described in U.S. Pat. No. 6,508,833 to Pavcnik for a MULTIPLE-SIDED INTRALUMINAL MEDICAL DEVICE.

Examples of suitable materials for the valve 14 include flexible materials, natural materials, synthetic materials, and combinations thereof. Examples of suitable natural materials include collagen, extracellular matrix (ECM) materials, such as submucosa, and other bioremodellable materials, such as bovine pericardium. Small intestine submucosa (SIS) is particularly well-suited for use as the graft members 14, 16. Other examples of ECM materials that can be used for the graft member include stomach submucosa, liver basement membrane, urinary bladder submucosa, tissue mucosa, and dura mater. ECMs are particularly well-suited materials for use in the graft member, at least because of their abilities to remodel and become incorporated into adjacent tissues. These materials can provide a scaffold onto which cellular in-growth can occur, eventually allowing the material to remodel into a structure of host cells. Examples of suitable synthetic materials include polymeric materials, such as polypropylene, polyurethane, and expanded polytetrafluoroethylene (ePTFE).

Tubular valves are also suitable for use in medical devices according to the invention. As best illustrated in FIG. 1, the valve 14 can comprise a valve formed at one end 34 of a tubular body 36. The valve 14 can be formed by forming valve portions 38, 40 on one end 34 of the tubular body 36. The valve portions 38, 40 can be formed by attaching the tubular body 36 to the main body 12 in the illustrated configuration, or in any other suitable configuration that forms valve portions 38, 40. Any suitable attachment element and/or technique can be used to attach the tubular body 36 to the main body 12 and to form the valve portions 38, 40, such as sutures, adhesives, bonding, and the like. The specific attachment element and/or technique chosen will depend on several factors, including the materials and form of the valve 14 and the main body 12.

FIGS. 2 and 3 illustrate the medical device 10 according to the first embodiment positioned within a body vessel 50. In FIG. 2, the valve 14 is in an open configuration. In this configuration, the valve 14 permits fluid flow through the passageway 22 in a first direction 32. In the closed configuration, illustrated in FIG. 3, the valve 14 substantially prevents fluid flow through the passageway 22 in a second, opposite direction 33. The valve 14 can alternate between the open and closed configurations. The mechanism by which the valve 14 alternates between these configurations will depend on the type of valve used. When a tubular valve is used, such as the valve 14 illustrated in FIGS. 1 through 3, the valve portions 38, 40 can move in response to changes in direction of fluid flow and/or fluid pressure to accomplish the transition from the open configuration to the closed configuration, and vice versa.

The vessel engaging member 16 provides a means for engaging a body vessel in which the medical device 10 is implanted. The vessel engaging member 16 defines an aperture 42 and has inner 44 and outer 46 edges. A dimension 48, such as a radial thickness, extends from the inner edge 44 to the outer edge 46. The main body 12 is disposed in the aperture 42. The vessel engaging member 16 substantially prevents fluid flow through the body vessel in which the device 10 is implanted apart from the fluid flow that moves through the valve 14. Accordingly, the vessel engaging member 16 is dimensioned and configured to have a suitable fit with the main body 12. Specifically, the aperture 42 should be dimensioned and configured to provide an appropriate fit between the vessel engaging member 16 and the main body 12. The fit should substantially prevent fluid flow through the interface between the member 16 and main body 12, and should be sufficiently stable to prevent any significant movement of the main body 12 relative to the vessel engaging member 16 under physiological conditions following implantation of the device 10 in a body vessel. To achieve an appropriate fit, the aperture 42 can be dimensioned such that friction between the member 16 and the main body 12 is sufficient. As illustrated in FIG. 1, a centrally-located aperture 42 of an appropriate dimension and configuration provides a suitable fit. To ensure an effective fit, the aperture 42 can have a diameter that is slightly smaller than an outer diameter of the main body 12. Also, the vessel engaging member 16 can be attached to the main body 12 in any appropriate manner, such as by adhesives or other bonding mechanisms.

The vessel engaging member 16 is also dimensioned and configured to have a suitable fit with the inner wall of a body vessel in which the device 10 is implanted. FIGS. 2 and 3 illustrate the medical device 10 of the first embodiment implanted within a body vessel 50. The outer edge 46 of the vessel engaging member 16 can be dimensioned and configured to mimic the surface of the inner wall 52 of the vessel 50. The devices of the present invention are particularly well suited for use as prosthetic venous valves. Accordingly, the vessel engaging member 16 can be dimensioned and configured to provide a suitable fit with the inner wall of an animal vein of interest. As illustrated in FIGS. 1 through 3, a disc-shaped vessel engaging member 16 provides a suitable configuration for use in veins.

To ensure a suitable fit between the vessel engaging member 16 and the body vessel 50, the vessel engaging member 16 can have a diameter that is slightly larger than an inner diameter of the body vessel 50 at a particular point of treatment. Animal veins, including human veins, have elastic properties and are able to alter their shape by expansion or other mechanisms to accommodate an appropriately-sized article implanted within the vein. A vessel engaging member 16 with a diameter slightly larger than an inner diameter of a vein in which the device 10 is being implanted will remain at a point of treatment within the vein due to friction between the vessel engaging member 16 and the inner wall of the vein. This dimensioning of the vessel engaging member 16 may also enhance the fit between the member 16 and the main body 12 due to compression of the inner edge 44 on the main body 12 arising from force exerted on the member 16 by the body vessel. The specific diameter chosen for the vessel engaging member 16 will depend on several factors, including the extent to which the vein at a particular point of treatment can alter its shape to accommodate the medical device 10.

Any suitable material can be used to form the vessel engaging member 16. The material chosen need only be biocompatible, or be able to be made biocompatible, and provide the desired properties described herein. The material chosen also should be substantially impervious to fluid flow through the material, unless it is desired to allow fluid flow through the body vessel independent of the valve 14. The specific material chosen for the vessel engaging member 16 will depend on several factors, including the environment in which the device 10 will be placed, the nature of the fluid(s) to which the device 10 will be exposed, the nature of the body vessel in which the device 10 will be implanted, and the desired delivery technique for implanting the device 10. Examples of suitable materials include synthetic materials, such as polymers, including polyurethane and polytetrafluoroethylene, and gels, and natural materials, such as ECM materials. Hydrogel materials are particularly well-suited for use in the vessel engaging member 16.

FIG. 4 illustrates a medical device 110 according to a second embodiment of the invention. The device 110 illustrated in FIG. 4 is similar to the device 10 illustrated in FIGS. 1 through 3, except as detailed below. Thus, the device 110 of this embodiment includes a main body 112, a valve 114, and a vessel engaging member 116. The main body 112 has a proximal 118 and a distal 120 end, and defines a passageway 122 extending between the ends 118, 120. An inner surface 124 of the main body 112 bounds the passageway 122, and an outer surface 126 defines the exterior of the main body 112. A graft member 130 is disposed on the main body 112 and defines an impervious portion 128 of the main body 112.

The valve 114 is disposed in the passageway 122 and is adapted to permit fluid flow through the passageway 122 in a first direction 132, and substantially prevent fluid flow through the passageway 122 in a second, opposite direction (not illustrated in FIG. 4). The valve 114 is formed at one end 134 of a tubular body 136, and includes valve portions 138, 140.

The vessel engaging member 116 is disposed on the outer surface 126 of the main body 112 and defines an aperture 142. The main body 112 is disposed in the aperture 142. The vessel engaging member 116 has inner 144 and outer 146 edges and a radial dimension 148 that extends from the inner 144 to the outer 146 edges. In this embodiment, the radial dimension 148 for any given pair of points on the inner 144 and outer 146 edges is different than the radial dimension for any different set of points on the edges 144, 146.

In this embodiment, the aperture 142 comprises an opening in the vessel engaging member that is continuous with the outer edge 146 of the vessel engaging member 116. This positioning of the aperture 142 allows the main body 112 to be positioned near an inner wall of a vessel in which the device 110 is implanted, which may be desirable to avoid a diseased portion of a vessel, to bypass a blockage of the vessel, or for other reasons.

FIG. 5 illustrates a sectional view of a medical device 210 according to a third embodiment of the invention within a body vessel 250. The device 210 illustrated in FIG. 5 is similar to the device 10 illustrated in FIGS. 1 through 3, except as detailed below. Thus, the device 210 of this embodiment includes a main body 212, a valve 214, and a vessel engaging member 216. The main body 212 has a proximal 218 and a distal 220 end, and defines a passageway 222 extending between the ends 218, 220. An inner surface 224 of the main body 212 bounds the passageway 222, and an outer surface 226 defines the exterior of the main body 212. A graft member 230 is disposed on the main body 212 and defines an impervious portion 228 of the main body 212.

The valve 214 is disposed in the passageway 222 and is adapted to permit fluid flow through the passageway 222 in a first direction (not illustrated in FIG. 5), and substantially prevent fluid flow through the passageway 222 in a second, opposite direction 233. The valve 214 is formed at an end 234 of a tubular body 236, and includes valve portions 238, 240.

The vessel engaging member 216 is disposed on the outer surface 226 of the main body 212 and defines an aperture 242. The main body 212 is disposed in the aperture 242. The vessel engaging member 216 has inner 244 and outer 246 edges and a radial dimension 248 that extends from the inner 244 to the outer 246 edges.

In this embodiment, the medical device 10 includes structural features 260 that pierce at least a portion of the wall of a body vessel 250. As used herein, the term "pierce" refers to a passing into a thickness of a wall of a body vessel. The thickness can be any partial or the complete thickness of the wall. The structural features 260 can comprise barbs, which are well known in the stent art. Also, the structural features 260 can be positioned on the vessel engaging member 216, as illustrated in FIG. 5, or at any other position on the medical device 210 that enables their interaction with the body vessel 250. Furthermore, any suitable number of structural features 260 can be included. In other embodiments, structural features that frictionally engage, but do not pierce, the vessel wall are includes in the medical device. For example, the outer surface of the vessel engaging member can define one or more raised bumps or indentations.

FIG. 6 illustrates a medical device 310 according to a fourth embodiment of the invention within a body vessel 350. The device 310 illustrated in FIG. 6 is similar to the device 10 illustrated in FIGS. 1 through 3, except as detailed below. Thus, the device 310 of this embodiment includes a main body 312, a valve 314, and a vessel engaging member 316. The main body 312 has a proximal 318 and a distal 320 end, and defines a passageway 322 extending between the ends 318, 320. An inner surface 324 of the main body 312 bounds the passageway 322, and an outer surface 326 defines the exterior of the main body 312. A graft member 330 is disposed on the main body 312 and defines an impervious portion 328 of the main body 312.

The valve 314 is disposed in the passageway 322 and is adapted to permit fluid flow through the passageway 322 in a first direction (not illustrated in FIG. 6), and substantially prevent fluid flow through the passageway 322 in a second, opposite direction 333. The valve 314 is formed at an end 334 of a tubular body 336, and includes valve portions 338, 340.

The vessel engaging member 316 is disposed on the outer surface 326 of the main body 312 and defines an aperture 342. The main body 312 is disposed in the aperture 342. The vessel engaging member 316 has inner 344 and outer 346 edges and a radial dimension 348 that extends from the inner 344 to the outer 346 edges.

In this embodiment, the vessel engaging member 316 defines an opening 362 adapted to permit a controlled amount 363 of fluid flow through the body vessel in the second, opposite direction 333. The controlled amount 363 of fluid flow is a portion of the fluid flow in the second, opposite direction 333. It may be desirable to permit this controlled amount 363 of fluid flow in the second, opposite direction 333 for a variety of reasons. For example, it may reduce, minimize or eliminate pooling of fluid in and around the device 310 during periods of closure of the valve 314.

As illustrated in FIG. 6, the vessel engaging member 316 can define a plurality of the openings 362. When a plurality of openings 362 is utilized, the openings 362 can be arranged in any suitable pattern. An equidistant spacing between all openings 362 provides a suitable pattern and may maximize the efficiency of moving the controlled amount 363 of fluid flow through the vessel engaging member 316.

The dimensions, configuration, and number of the openings 362 can be optimized based upon the vessel in which the device 310 is implanted. The size and configuration selected will depend on several factors, including the vessel size, typical flow volumes and rates, and others. The opening 362 should be sized to allow a desired amount flow in the second, opposite direction to occur, while remaining sufficiently small to still allow the medical device 310 to act as a valve. Thus, the opening 362 can be sized so as not to allow a majority of retrograde flow to pass through the opening.

The opening 362 can be sized to mimic the degree of retrograde flow—the leakiness—that flows through a natural valve located at or near the point of treatment. In these embodiments, the dimensions of the opening 362 can be determined and optimized based upon the vessel in which the device 310 is to be placed. For example, in prosthetic venous valve embodiments, the total open area of the opening 362 can be less than about 50% of the cross-sectional area of the vessel, or less than about 25% of the total cross-sectional area of the vessel. In one example, a device is configured for placement in a vessel having a total cross-sectional area of about 50 mm². In this example, the opening 362 has a total open area of about 10 mm².

In devices including multiple openings 362 that permit a controlled amount 363 of fluid flow in the second, opposite direction 333 to flow through the vessel in which the device 310 is implanted, the total open area of all openings 362 can be optimized as described above, but it is not necessary that the individual openings 362 have open areas of the same size.

FIG. 7 illustrates a medical device 410 according to a fifth embodiment of the invention within a body vessel 450. The device 410 illustrated in FIG. 7 is similar to the device 10 illustrated in FIGS. 1 through 3, except as detailed below. Thus, the device 410 of this embodiment includes a main body 412, a valve 414, and a vessel engaging member 416. The main body 412 has a proximal (not illustrated in FIG. 7) and a distal 420 end, and defines a passageway 422 extending between the ends 418, 420. An inner surface 424 of the main body 412 bounds the passageway 422, and an outer surface 426 defines the exterior of the main body 412. A graft member 430 is disposed on the main body 412 and defines an impervious portion 328 of the main body 312.

The valve 414 is disposed in the passageway 422 and is adapted to permit fluid flow through the passageway 422 in a first direction 432, and substantially prevent fluid flow through the passageway 422 in a second, opposite direction (not illustrated in FIG. 7). The valve 414 is formed at one end 434 of a tubular body 436, and includes valve portions 438, 440.

The vessel engaging member 416 is disposed on the outer surface 426 of the main body 412. The vessel engaging member 416 has first 470 and second 472 ends. The first end 472 defines a first opening 474 having a first inner diameter, and the second end 472 defines a second opening 476 having a second inner diameter. The first inner diameter is greater than the second inner diameter. The second end 472 is disposed on the outer surface 426 of the main body. This configuration of the vessel engaging member 416 provides a manifold that collects fluid flowing through the body vessel 450 in the first direction 432 and directs the flow into the main body 412 and toward the valve 414. A graft material, such as SIS and other bioremodellable materials, is particularly well-suited for use as the vessel engaging member 416 in medical devices according to this embodiment of the invention.

FIG. 8 illustrates a medical device 510 according to a sixth embodiment of the invention within a body vessel 550. The device 510 illustrated in FIG. 8 is similar to the device 410 illustrated in FIG. 7, except as detailed below. Thus, the device 510 of this embodiment includes a main body 512, a valve 514, and a vessel engaging member 516. The main body 512 has proximal and distal ends (not illustrated in FIG. 8), and defines a passageway 522 extending between the ends. An inner surface 524 of the main body 512 bounds the passageway 522, and an outer surface 526 defines the exterior of the main body 512. A graft member 530 is disposed on the main body 512 and defines an impervious portion 528 of the main body 512.

The valve 514 is disposed in the passageway 522 and is adapted to permit fluid flow through the passageway 522 in a first direction 532, and substantially prevent fluid flow through the passageway 522 in a second, opposite direction (not illustrated in FIG. 8). The valve 514 is formed at an end 534 of a tubular body 536, and includes valve portions 538, 540.

In this embodiment, the medical device 510 includes first 516 and second 580 vessel engaging members. Both vessel engaging member 516, 580 are disposed on the outer surface 526 of the main body 512. The first vessel engaging member 516 has first 570 and second 572 ends. The first end 572 defines a first opening 574 having a first inner diameter, and the second end 572 defines a second opening 576 having a second inner diameter. The first inner diameter is greater than the second inner diameter. The second end 572 is disposed on the outer surface 526 of the main body. This configuration of the first vessel engaging member 516 provides a manifold that collects fluid flowing through the body vessel 550 in the first direction 532 and directs the flow into the main body 512 and toward the valve 514.

The second vessel engaging member 580 has third 582 and fourth 584 ends. The third end defines a third opening 586 having a third inner diameter, and the fourth end 584 defines a fourth opening 588 having a fourth inner diameter. The third inner diameter is greater than the fourth inner diameter. The fourth end 584 is disposed on the outer surface 526 of the main body 512. This configuration of the second vessel engaging member 580 provides a manifold that directs fluid exiting the valve 514 and main body 512 into the body vessel 550.

The first 516 and second 580 vessel engaging members create a void region 590 in the vessel 550. The void region 590 is excluded from the flow pattern of fluid through the vessel 550 due to the configuration of the device 510. The void region 590 can be used for anchoring the device 510 to the vessel 550, such as by structural features discussed above, or by sutures or other securement means applied to the exterior of the vessel 550. Also, the void region 590 can be used to exclude a portion of the body vessel 550 from fluid flow, such as a diseased portion of the vessel 550.

FIG. 9 illustrates a delivery device 600 according to an embodiment of the invention. The delivery device 600 comprises a suitable elongate member 602 known to those skilled in the art. The elongate member 602 has a distal tip 604 and defines an external surface 606. A medical device 610 according to the present invention is disposed on the distal tip 604 by passing the tip 604 through the passageway 622 of the main body 612 of the device 610. The delivery device 600 can include a sheath 608 disposed over the elongate member 602. The sheath 608 is a hollow member that defines a lumen 609 that receives the elongate member 602. The sheath 608 can be disposed over the medical device 610 to maintain the device 610 in a radially compressed configuration. In this configuration, the vessel engaging member 616 is compressed between the sheath 608 and the main body 612 of the medical device 610. In this arrangement, the catheter 600 can be navigated through a body vessel according to techniques well known in the art. Once the medical device is positioned at a point of treatment, the sheath 608 can be withdrawn to allow the medical device to change to a radially expanded configuration. Following the deployment of the medical device 610, the catheter can be withdrawn from the point of treatment, leaving the medical device 610 implanted. If the medical device 610 is a balloon expandable device, the elongate member 602 can define an inflation lumen for a balloon on which the medical device 610 is mounted, as is known in the art.

Further, the elongate member 602 can define a guidewire lumen 607 that facilitates navigation of the member 602 through a body vessel by accommodating a previously placed guidewire. If included, the guidewire lumen 607 can extend along the entire length of the elongate member 602, or only along a portion of the length, as in a rapid exchange arrangement known in the art. A catheter according to this aspect of the invention can facilitate placement of multiple prosthetic valves in a single vessel by allowing for rapid exchange of one catheter carrying a medical device according to the invention for another without removal of a previously placed guidewire. This may be particularly desirable in prosthetic venous valve embodiments because it may be desirable to place two or more such devices in a single vessel during a single treatment.

Figure 10:
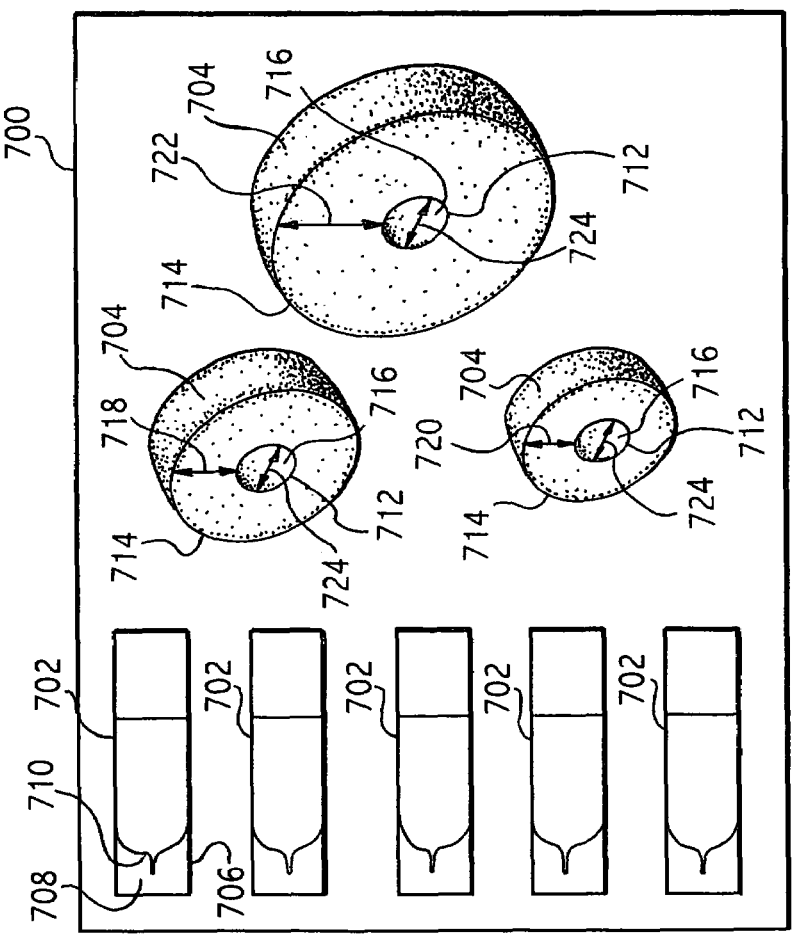
FIG. 10 is a schematic illustrating a kit according to an embodiment of the invention.

FIG. 10 illustrates a kit 700 according to the invention. The kit 700 comprises a valve member 702 and a plurality of vessel engaging members 704. The valve member 702 comprises a main body 706 defining a passageway 708 and a valve 710 disposed in the passageway 708 and can be any suitable main body and valve combination according to the invention, including those detailed in the context of exemplary embodiments above. The valve 710 is adapted to permit fluid flow through the passageway 708 in a first direction, and substantially prevent fluid flow through the passageway 708 in a second, opposite direction. As illustrated in FIG. 10, the kit 700 can include a plurality of valve members 702. Also, the kit 700 can further include a catheter to facilitate implantation of the medical device.

Each vessel engaging member 704 has inner 712 and outer 714 edges, and defines an aperture 716 adapted to receive a valve member 702. Also, each vessel engaging member defines a radial dimension extending between its inner 712 and outer 714 edges.

Two of the plurality of vessel engaging members 704 have different radial dimensions extending between their respective inner 712 and outer 714 edges. The kit illustrated in FIG. 10 includes three vessel engaging members 704 having three different dimensions 718, 720, and 722. Also, the vessel engaging members 704 of the kit 700 illustrated in FIG. 10 all have apertures 716 of the same diameter 724. If a plurality of valve members is included in a kit, and two valve members have main bodies of different outer diameters, the diameters of the apertures 716 could be varied in a manner similar to that of the radial dimensions 718, 720, 722.

A medical device in accordance with the present invention can be made by disposing a valve member 702 in the aperture 716 of one of the plurality of vessel engaging members 704. The kit 700 allows a user to assemble a medical device according to the present invention with a dimension suitable for an application of interest. For example, a clinician can assemble a medical device having a vessel engaging member 704 with a dimension appropriate for implantation of the device in a vein of a patient. The dimension can be determined by determining the inner diameter of the vein at a point of treatment.

The invention also provides methods of treating a patient. FIG. 11 provides a flow chart illustrating one method 800 according to the invention. In this method, step 802 comprises providing a kit according to the invention. Another step 804 comprises determining an inner diameter of a body vessel at a point of treatment. This step can be accomplished by any appropriate vessel sizing technique known in the art. Another step 806 comprises selecting a suitable vessel engaging member from the plurality of vessel engaging members in the kit. The selected vessel engaging member must have a dimension that is appropriate for the treatment based upon the inner diameter determined in step 804. The selection of an appropriate vessel engaging member can take into account the ability of the vessel to alter its shape to accommodate an implanted article, as explained above. Another step 808 comprises disposing the main body of a selected valve member from the kit in the aperture of the selected vessel engaging member to form a medical device according to the invention. Another step 810 comprises implanting the assembled medical device at the point of treatment in the body vessel. A step 812 of percutaneously delivering the medical device to the point of treatment can also be included. Step 812 can be accomplished by appropriate percutaneous techniques known in the art.

The foregoing description of exemplary embodiments of the invention includes the best mode for practicing the invention. It is intended to aid in the understanding of the invention, and not to limit the invention or its protection in any manner.

We claim:

1. A medical device for implantation in a body vessel, comprising:
   a tubular main body having an outer diameter, defining a passageway and comprising an outer surface having a portion that is impervious to fluid flow;
   a valve disposed in the passageway and adapted to permit fluid flow through the passageway in a first direction and substantially prevent fluid flow through the passageway in a second, opposite direction, the valve having a proximal end, a distal end, and an axial length; and a compressible vessel engaging member disposed on the outer surface of the main body and adapted to substantially prevent fluid flow through the body vessel in the second, opposite direction, the vessel engaging member having first and second opposing surfaces, an inner edge, an aperture defined by the inner edge and extending coaxially with the main body from the first surface to the second surface, an outer edge, and a radial thickness extending from the inner edge to the outer edge;

wherein the main body is disposed through the aperture and extends axially beyond the first and second surfaces of the vessel engaging member and axially beyond the proximal and distal ends of the valve, and the portion of the outer surface of the main body that is impervious to fluid flow extends at least along the axial length of the valve; and wherein the vessel engaging member has an expanded configuration in which the radial thickness of the vessel engaging member is larger than the outer diameter of the main body;

wherein the vessel engaging member further comprises a bioremodellable material; and wherein the main body further comprises a self-expanding support frame.

2. The medical device of claim 1, wherein the aperture is centrally disposed on the vessel engaging member.

3. The medical device of claim 1, wherein the vessel engaging member comprises one or more structural features adapted to engage said body vessel.

4. The medical device of claim 3, wherein the one or more structural features comprise a barb.

5. The medical device of claim 1, wherein the vessel engaging member comprises an opening that permits a controlled amount of fluid flow through said body vessel in the second, opposite direction.

6. The medical device of claim 1, wherein the vessel engaging member comprises a plurality of openings, each of the plurality of openings individually adapted to permit a controlled amount of fluid flow through said body vessel in the second, opposite direction.

7. The medical device of claim 6, wherein the plurality of openings are positioned equidistant from each other on the vessel engaging member.

8. The medical device of claim 1, wherein the vessel engaging member comprises a disc-shaped member.

9. The medical device of claim 1, wherein the vessel engaging member comprises a hydrogel.

10. The medical device of claim 1, wherein the vessel engaging member comprises an extracellular matrix material.

11. The medical device of claim 1, wherein the vessel engaging member comprises small intestine submucosa.

12. The medical device of claim 1, wherein the valve comprises a leaflet attached to the main body.

13. The medical device of claim 12, wherein the leaflet is adapted to move between a first position to permit fluid flow through the passageway in the first direction and a second position to substantially prevent fluid flow through the passageway in the second, opposite direction.

14. The medical device of claim 12, wherein the valve further comprises a second leaflet attached to the main body.

15. The medical device of claim 14, wherein the first and second leaflets individually move between first and second positions to cooperatively permit fluid flow through the passageway in the first direction and substantially prevent fluid flow through the passageway in the second, opposite direction.

16. The medical device of claim 12, wherein the leaflet comprises a bioremodellable material.

17. The medical device of claim 12, wherein the leaflet comprises an extracellular matrix material.

18. The medical device of claim 12, wherein the vessel engaging member comprises small intestine submucosa.

19. The medical device of claim 14, wherein the first and second leaflets comprise small intestine submucosa.

20. The medical device of claim 1, wherein the vessel engaging member also has a compressed configuration in which the radial thickness of the vessel engaging member is smaller than the outer diameter of the main body.

* * * * *

UNITED STATES PATENT AND TRADEMARK OFFICE
CERTIFICATE OF CORRECTION

PATENT NO.      : 7,628,804 B2
APPLICATION NO. : 10/857403
DATED           : December 8, 2009
INVENTOR(S)     : Flagle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1115 days.

Signed and Sealed this

Second Day of November, 2010

David J. Kappos
*Director of the United States Patent and Trademark Office*